US006346545B1

(12) United States Patent
Maier et al.

(10) Patent No.: US 6,346,545 B1
(45) Date of Patent: Feb. 12, 2002

(54) URETHANES, THIO AND DITHIO ANALOGUES AND THEIR USE AS INHIBITORS OF CHOLESTEROL BIOSYNTHESIS

(75) Inventors: Roland Maier; Rudolf Hurnaus; Michael Mark; Bernhard Eisele, all of Biberach (DE); Peter Mueller, Stamford, CT (US); Gebhard Adelgoss, Biberach; Gebhard Schilcher, Mittelbiberach, both of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/275,318

(22) Filed: Mar. 24, 1999

Related U.S. Application Data

(60) Provisional application No. 60/073,050, filed on Jan. 29, 1998.

(30) Foreign Application Priority Data

Dec. 10, 1997 (DE) .......................... 197 54 795

(51) Int. Cl.$^7$ ...................... A61K 31/27; C07C 269/04
(52) U.S. Cl. ...................... 514/478; 514/481; 514/484; 560/19; 560/115
(58) Field of Search ................ 514/478, 481, 514/484; 560/19, 115

(56) References Cited

U.S. PATENT DOCUMENTS

| | | | |
|---|---|---|---|
| 5,011,859 A | * 4/1991 | Jarvi et al. ................ 514/739 |
| 5,084,461 A | * 1/1992 | Wannamaker et al. ...... 514/307 |
| 5,455,273 A | 10/1995 | Maier et al. |
| 5,466,687 A | 11/1995 | Maier et al. |
| 5,726,205 A | 3/1998 | Woitun et al. |

FOREIGN PATENT DOCUMENTS

| | | |
|---|---|---|
| DE | 42 39 151 A | 5/1994 |
| DE | 4438020 | * 10/1994 |
| DE | 44 38 020 A | 5/1996 |
| EP | 420116 | * 4/1991 |
| EP | 468434 | * 1/1992 |
| EP | 0 596 326 A | 5/1994 |
| WO | WO95/29148 | 11/1995 |

OTHER PUBLICATIONS

Bundgaard "Design of prodrugs" Elsevier pp.27–33, 1986.*
Mark et al. "Effects of a novel 2,3–oxidosqualene cyclase inhibitor . . . " J. Lip. Res. v.37, pp.148–158, 1996.*

* cited by examiner

Primary Examiner—Ceila Chang
(74) Attorney, Agent, or Firm—R. P. Raymond; T. X. Witkowski; A. R. Stempel

(57) ABSTRACT

The present invention relates to urethanes and the thio and dithio analogues thereof of general formula

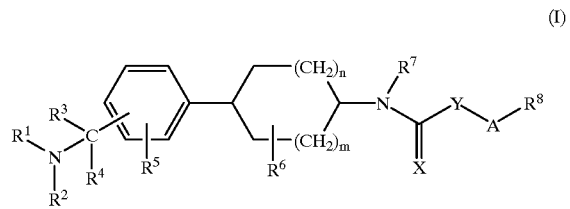

(I)

wherein m, n, A, X, Y and $R^1$ to $R^8$ are defined as in claim 1, the enantiomers, diastereomers and the salts thereof, particularly the physiologically acceptable acid addition salts thereof which have valuable properties, particularly an inhibitory effect on cholesterol biosynthesis, pharmaceutical compositions containing these compounds, their use and processes for preparing them.

19 Claims, No Drawings

URETHANES, THIO AND DITHIO ANALOGUES AND THEIR USE AS INHIBITORS OF CHOLESTEROL BIOSYNTHESIS

This application claims benefit of provisional application No. 60/073050, filed Jan. 29, 1998.

The present invention relates to new urethanes, the thio and dithio analogues thereof, the salts thereof with physiologically acceptable organic and inorganic acids, processes for preparing these compounds and pharmaceutical compositions containing them.

The compounds according to the invention are inhibitors of cholesterol biosynthesis, particularly inhibitors of the enzyme 2,3-epoxysqualene-lanosterol-cyclase, a key enzyme in cholesterol biosynthesis. The compounds according to the invention are suitable for the treatment and prophylaxis of hyperlipidaemias, hypercholesterolaemias and atherosclerosis. Other possible applications are in the treatment of hyperproliferative skin and vascular diseases, tumours, gallstone problems and mycoses.

Compounds which affect cholesterol biosynthesis are important for the treatment of a number of diseases. These include in particular hypercholesterolaemias and hyperlipidaemias which are risk factors for the occurrence of atherosclerotic vascular changes and their sequelae such as coronary heart disease, cerebral ischaemia, Claudicatio intermittens and gangrene.

The significance of elevated serum-cholesterol levels as a main risk factor for the occurrence of atherosclerotic vascular changes is generally known. Extensive clinical studies have led to the finding that the risk of developing coronary heart diseases can be reduced by lowering serum cholesterol (Current Opinion in Lipidology 2(4), 234 [1991]; Exp. Opin. Ther. Patents 7(5), 441–455 [1997]). Since the majority of the cholesterol is synthesised in the body itself and only a small proportion is taken in with the food, inhibiting biosynthesis is a particularly attractive method of lowering raised cholesterol levels.

In addition, other possible applications for cholesterol biosynthesis inhibitors are the treatment of hyperproliferative skin and vascular diseases and tumours, the treatment and prophylaxis of gallstone problems and their use in treating mycoses. The latter case involves intervening in the ergosterol biosynthesis in fungal organisms which proceeds substantially analogously to cholesterol biosynthesis in mammalian cells.

The cholesterol or ergosterol biosynthesis takes place, starting from acetic acid, via a large number of reaction steps. This multi-stage process offers a number of possible interventions, of which the following are examples:

For inhibiting the enzyme 3-hydroxy-3-methylglutaryl-coenzyme A (HMG-CoA)-synthase, β-lactones and β-lactams with a potential antihypercholesterolaemic activity are mentioned (cf. J. Antibiotics 40, 1356 [1987], U.S. Pat. No. 4,751,237, EP-A-0 462 667, U.S. Pat. No. 4,983, 597).

Examples of inhibitors of the enzyme HMG-CoA-reductase are 3,5-dihydroxycarboxylic acids of the mevinolin type and their δ-lactones, of which lovastatin, simvastatin, pravastatin, fluvastatin, atorvastatin and cerivastatin are used in the treatment of hypercholesterolaemias. Other possible applications for these compounds are fungal infections (U.S. Pat. No. 4,375,475, EP-A-0 113 881, U.S. Pat. No. 5,106,992), skin diseases (EP-A-0 369 263) and gallstone problems and tumour diseases (U.S. Pat. No. 5,106,992; Lancet 339, 1154–1156 [1992]).

The inhibition of the proliferation of smooth muscle cells by lovastatin is described in Cardiovasc. Drugs. Ther. 5, Suppl. 3, 354 [1991]. Tocotrienol, an unsaturated analogue of vitamin E, and its analogues make up another class of substances which act on HMG-CoA-reductase (Exp. Opin. Ther. Patents 7 (5), 446 [1997]).

Inhibitors of the enzyme squalene-synthetase are e.g. isoprenoid-(phosphinylmethyl)-phosphonates, the suitability of which for treating hypercholesterolaemias, gallstone problems and tumour diseases is described in EP-A-0 409 181 and in J. Med. Chemistry 34, 1912 [1991], and also α-phosphonosulfinate compounds (EP-A-0 698 609), the compounds J-104,118 and J-104,123 (Tetrahedron 52, 13881–13894, [1996]) and cyclobutane derivatives (WO 96/33159). A survey of squalene-synthethase inhibitors can be found in Exp. Opin. Ther. Patents 7 (5), 446–448 [1997].

Known inhibitors of the enzyme squalene-epoxidase are allylamines such as naftifine and terbinafine, which have been used in therapy to fight fungal diseases, and also the allylamine NB-598 with an antihypercholesterolaemic activity (J. Biol. Chemistry 265, 18075–18078 [1990]) and fluorosqualene derivatives with a hypocholesterolaemic activity (U.S. Pat. No. 5,011,859). Moreover, piperidines and azadecalines with a potential hypocholesterolaemic and/or antifungal activity are described, the mechanism of activity of which has not been fully explained and which are squalene epoxidase and/or 2,3-epoxisqualene-lanosterol-cyclase inhibitors (EP-A-0 420 116, EP-A-0 468 434, U.S. Pat. No. 5,084,461 and EP-A-0 468 457). Other examples are described in Exp. Opin. Ther. Patents 7 (5), 448–449 [1997].

Examples of inhibitors of the enzyme 2,3-epoxisqualene-lanosterol-cyclase are diphenyl derivatives (EP-A-0 464 465), aminoalkoxybenzene derivatives (EP-A-0 410 359, J. Lipid. Res. 38, 373–390, [1997]) and piperidine derivatives (J. Org. Chem. 57, 2794–2903 [1992] which have an antifungal activity. Moreover this enzyme is inhibited in mammalian cells by decalines, azadecalines and indane derivatives (WO 89/08450; J. Biol. Chemistry 254, 11258–11263 [1981]; Biochem. Pharmacology 37, 1955–1964 [1988] and J 64 003 144), and also by 2-aza-2,3-dihydro-squalene and 2,3-epiminosqualene (Biochem. Pharmacology 34, 2765–2777 [1985]), by squalenoid-epoxide-vinylether (J. Chem. Soc. Perkin Trans. I, 461 [1988]) and 29-methylidene-2,3-oxidosqualene (J. Amer. Chem. Soc. 113, 9673–9674 [1991]). Other examples are pyridine and pyrimidine derivatives (WO 97/06802), heterobicyclic alkylamines (WO 96/11201), imidazole derivatives (EP-A-0 757 988) and isoquinoline derivatives (J. Med. Chemistry 39, 2302–2312, [1996]). Other compounds described are ureas (DE-A-4 438 021) oximes (DE-A-4 412 692), a number of amides (DE-A-4 407 134, DE-A-4 407 135, DE-A-4 407 136, DE-A-4 407 138, DE-A-4 407 139, DE-A-4 412 691, DE-A-4 437 999, DE-A-4 438 000, DE-A-4 438 020, DE-A-4 438 082, DE-A-4 438 029, DE-A-4 438 054, DE-A-4 438 055, DE-A-4 438 082, DE-A-4 438 083, EP-A-0 599 203, EP-A-0 596 326) and esters (WO 95/29148). Other examples are described in Exp. Opin. Ther. Patents 7(5), 448–449 [1997].

Finally, inhibitors of the enzyme lanosterol-14α-demethylase also include steroid derivatives with a potential antihyperlipidaemic activity which simultaneously influence the enzyme HMG-CoA-reductase (U.S. Pat. No. 5,041,431; J.Biol. Chemistry 266, 20070–20078 [1991]; U.S. Pat. No. 5,034,548). This enzyme is also inhibited by the antimycotics of the azole type which constitute N-substituted imidazoles and triazoles. This class includes, for example, the commercially available antimycotics ketoconazole and fluconazole.

The compounds of the following general formula I are new. It has been found that, surprisingly, they are highly effective inhibitors of the enzyme 2,3-epoxisqualene-lanosterol-cyclase (International Classification: EC 5.4.99.7).

The enzyme 2,3-epoxisqualene-lanosterol-cyclase catalyses a key step of cholesterol or ergosterol biosynthesis, namely the conversion of 2,3-epoxisqualene into lanosterol, the first compound with a steroid structure in the biosynthesis cascade. Inhibitors of this enzyme lead one to expect the advantage of higher selectivity, compared with inhibitors of earlier stages of biosynthesis, such as for example HMG-CoA-synthase and HMG-CoA-reductase, since inhibiting these early stages of biosynthesis leads to a reduction in biosynthetically formed mevalonic acid and consequently may have a negative effect on the biosynthesis of the mevalonic acid-dependent substances dolichol, ubiquinone and isopentenyl-t-RNA (cf. J. Biol. Chemistry 265, 18075–18078 [1990].

When stages of biosynthesis after the conversion of 2,3-epoxysqualene into lanosterol are inhibited, there is a risk of the accumulation of intermediate products with a steroid structure in the body and the triggering of toxic effects caused by them. This has been described, for example, in the case of triparanol, a desmosterol-reductase inhibitor. This substance had to be taken off the market on account of the formation of cataracts, ichthyosis and alopecia (mentioned in J. Biol. Chemistry 265, 18075–18078 [1990]).

As already stated hereinbefore, inhibitors of 2,3-epoxisqualene-lanosterol-cyclase have already been described in the literature. However, absolutely no urethanes or their thio or dithio analogues are known as inhibitors of 2,3-epoxisqualene-lanosterol-cyclase.

The invention relates to the preparation of antihypercholesterolaemic substances which are suitable for the treatment and prophylaxis of atherosclerosis and are distinguished from known active substances by their superior antihypercholesterolaemic activity with greater selectivity and hence greater safety. Since the compounds according to the invention are also able to inhibit ergosterol biosynthesis in fungal organisms by virtue of their great efficacy as inhibitors of the enzyme 2,3-epoxisqualene-lanosterol-cyclase, they are also suitable for treating mycoses.

The present invention relates to the new urethanes and the thio and dithio analogues thereof of general formula

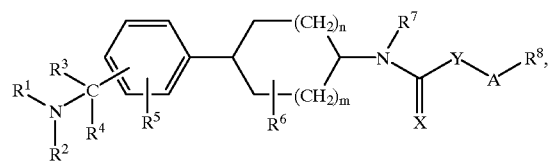

(I)

wherein
  m denotes the numbers 0 or 1,
  n denotes the numbers 1 or 2,
  A denotes a single bond, a straight-chained or branched $C_{1-8}$-alkylene group, a $C_{2-8}$-alkenylene or $C_{2-8}$-alkynylene group, whilst an unsaturated group is not directly bound to the group Y,
  X denotes an oxygen or sulphur atom,
  Y denotes an oxygen or sulphur atom,
  $R^1$ denotes a straight-chained or branched $C_{1-8}$-alkyl group, a $C_{1-6}$-alkenyl group or a $C_{1-6}$-alkynyl group, whilst the multiple bond is isolated from the nitrogen-carbon bond,
  $R^2$ denotes a hydrogen atom, a straight-chained or branched $C_{1-8}$-alkyl group which may be substituted by a hydroxy or alkoxy group, a $C_{1-6}$-alkenyl group or a $C_{1-6}$-alkynyl group, whilst a hydroxy and alkoxy substituent is not bound in the 1-position and a multiple bond is isolated from the nitrogen-carbon bond, or
  $R^1$ and $R^2$ together with the nitrogen atom denote a 5- to 7-membered, saturated heterocyclic ring wherein a methylene group isolated from the nitrogen atom may be replaced by an oxygen or sulphur atom or by an —NH— or —N(alkyl)- group,
  $R^3$ to $R^6$, which may be identical or different, denote hydrogen atoms or alkyl groups,
  $R^7$ denotes a straight-chained or branched $C_{1-6}$-alkyl group, a $C_{1-6}$-alkenyl group or a $C_{1-6}$-alkynyl group, whilst the multiple bond is isolated from the nitrogen-carbon bond,
  $R^8$ denotes a $C_{3-7}$-cycloalkyl group, a phenyl or naphthyl group optionally substituted by one or two halogen atoms or by an alkyl, alkoxy, trifluoromethyl or cyano group or, if A does not denote a single bond, $R^8$ also denotes a hydrogen atom,
  whilst, unless otherwise stated, alkyl groups contained in the groups mentioned above may contain 1 to 3 carbon atoms and a halogen atom mentioned above may be a fluorine, chlorine or bromine atom,
  the enantiomers, diastereomers, the mixtures thereof and the salts thereof, particularly the physiologically acceptable acid addition salts thereof.

The preferred compounds are the compounds of general formula I, wherein
  m denotes the number 1,
  n denotes the number 1,
  A denotes a single bond, a straight-chained or branched $C_{1-6}$-alkylene group,
  X denotes an oxygen or sulphur atom,
  Y denotes an oxygen or sulphur atom,
  $R^1$ denotes a straight-chained or branched $C_{1-6}$-alkyl group,
  $R^2$ denotes a hydrogen atom, a straight-chained or branched $C_{1-6}$-alkyl group which may be substituted by a hydroxy group, a $C_{1-4}$-alkenyl group or a $C_{1-4}$-alkynyl group, whilst the hydroxy group is not bound in the 1 position and the multiple bond is isolated from the nitrogen-carbon bond, or $R^1$ and $R^2$ together with the nitrogen atom denote a 5- to 7-membered, saturated heterocyclic ring wherein a methylene group isolated from the nitrogen atom may be replaced by an oxygen atom, $R^3$ to $R^6$, which may be identical or different, denote hydrogen atoms or methyl groups, $R^7$ denotes a straight-chained or branched $C_{1-6}$-alkyl group or a $C_{1-4}$-alkenyl group, whilst the multiple bond is isolated from the nitrogen-carbon bond, $R^8$ denotes a $C^{3-6}$-cycloalkyl group, a phenyl or naphthyl group optionally substituted by one or two halogen atoms or by an alkyl, alkoxy, trifluoromethyl or cyano group or, if A does not denotes a single bond, $R^8$ also denotes a hydrogen atom, whilst, unless otherwise stated, alkyl groups contained in the groups mentioned above may each contain 1 to 3 carbon atoms and a halogen atom mentioned above may be a fluorine, chlorine or bromine atom, the enantiomers, diastereomers, the mixtures thereof and the salts thereof, particularly the physiologically acceptable acid addition salts thereof.

Particularly preferred are the compounds of general formula I, wherein m denotes the number 1, n denotes the number 1, A denotes a single bond or a methylene group, X denotes an oxygen or sulphur atom, Y denotes an oxygen or sulphur atom, $R^1$ denotes a methyl or ethyl group, $R^2$ denotes a methyl, ethyl, allyl or propargyl group or $R^1$ and $R^2$ together with the nitrogen atom denote a pyrrolidine or piperidine ring, $R^3$ to $R^6$ denote hydrogen atoms, $R^7$ denotes a methyl group, $R^8$ denotes a phenyl group optionally substituted by a chlorine or fluorine atom or by a methyl group, the mixtures and the salts thereof, particularly the physiologically acceptable acid addition salts thereof, but particularly the compounds (1) trans-S-(4-chlorophenyl)-N-4-[4-(dimethylaminomethyl)-phenyl]cyclohexyl-N-methyldithiocarbamate, (2) trans-S-(3-fluorobenzyl)-N-4-[4-(dimethylaminomethyl)-phenyl]cyclohexyl-N-methyldithiocarbamate, (3) trans-S-(4-fluorobenzyl)-N-4-[4-(dimethylaminomethyl)-phenyl]cyclohexyl-N-methyldithiocarbamate, (4) trans-S-(4-chlorobenzyl)-N-4-[4-(dimethylaminomethyl)-phenyl]cyclohexyl-N-methyldithiocarbamate, (5) trans-O-(4-chlorophenyl)-N-4-[4-(dimethylaminomethyl)-phenyl]cyclohexyl-N-methylcarbamate, (6) cis-S-benzyl-N-4-[4-(dimethylaminomethyl)phenyl]-cyclohexyl-N-methyldithiocarbamate, (7) trans-O-(4-chlorophenyl)-N-4-[4-(dimethylaminomethyl)-phenyl]cyclohexyl-N-methylthiocarbamate, (8) trans-S-(4-chlorophenyl)-N-4-[4-(dimethylaminomethyl)-phenyl]cyclohexyl-N-methylthiocarbamate, (9) trans-O-(4-chlorophenyl)-N-methyl-N-4-[4-(piperidino-methyl)phenyl]cyclohexylcarbamate,

(10) trans-O-(4-chlorophenyl)-N-methyl-N-4-[4-(pyrrolidino-methyl)phenyl]cyclohexylcarbamate,

(11) trans-O-(4-chlorophenyl)-N-4-[4-(diethylaminomethyl)-phenyl]cyclohexyl-N-methylcarbamate,

(12) trans-O-(4-chlorophenyl)-N-methyl-N-4-[4-(N-methyl-N-allylaminomethyl)phenyl]cyclohexylcarbamate,

(13) trans-O-(4-chlorophenyl)-N-methyl-N-4-[4-(N-methyl-N-propargylaminomethyl)phenyl]cyclohexylcarbamate,

(14) trans-N-4-[4-(dimethylaminomethyl)phenyl]cyclohexyl-N-methyl-O-(4-methylphenyl)carbamate,

(15) trans-N-4-[4-(dimethylaminomethyl)phenyl]cyclohexyl-N-methyl-O-(4-methylphenyl)thiocarbamate,

(16) trans-N-Methyl-O-(4-methylphenyl)-N-4-[4-(piperidinomethyl)phenyl]cyclohexylthiocarbamate and

(17) trans-N-4-[4-(dimethylaminomethyl)phenyl]cyclohexyl-O-(4-fluorophenyl)-N-methylcarbamate, the mixtures and the salts thereof, particularly the physiologically acceptable acid addition salts thereof, such as the hydrochlorides, methanesulphonates or tartrates thereof.

The compounds of general formula I may be prepared for example by the following methods:

a) reacting a compound of general formula

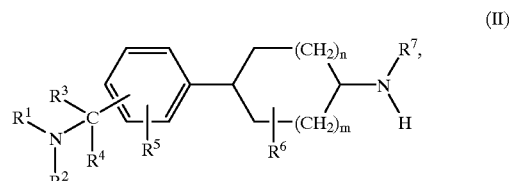

(II)

wherein m, n and $R^1$ to $R^7$ are as hereinbefore defined, with a compound of general formula

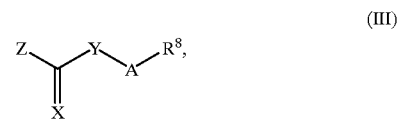

(III)

wherein

A, X, Y and $R^8$ are as hereinbefore defined and Z denotes a leaving group, e.g. a halogen atom such as the chlorine, bromine or iodine atom, and, if necessary, subsequently cleaving any protecting groups.

The reaction is carried out under Schotten-Baumann or Einhorn conditions, i.e. the components are reacted in the presence of at least one equivalent of an auxiliary base at temperatures of between −50°C. and +120° C., preferably −10° C. and +30° C., and optionally in the presence of solvents. Preferred auxiliary bases are alkaline and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, and tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, whilst preferred solvents include, for example, diethylether, methylene chloride, dichloromethane, ethyl acetate, toluene, tetrahydrofuran, 1,4-dioxane, acetonitrile, dimethylformamide, dimethylacetamide, N-methyl-pyrrolidone or mixtures thereof; if alkali or alkaline earth metal hydroxides, alkali metal carbonates or acetates are used as auxiliary bases, water may also be added to the reaction mixture as a cosolvent.

If $R^2$ denotes a hydrogen atom, the reaction is conveniently carried out by first reacting a compound of general formula (II), wherein $R^2$ denotes a protecting group, such as, preferably, the tert.butyloxycarbonyl group and, after the reaction has ended, cleaving the protecting group by conventional methods, e.g. by the action of trifluoroacetic acid or hydrogen chloride in dioxane.

b) In order to prepare compounds of general formula (I), wherein X and Y each denote a sulphur atom and m, n, A and $R^1$ to $R^8$ are as hereinbefore defined with the proviso that $R^8$ does not represent an optionally substituted phenyl or naphthyl group if A denotes a single bond:

reacting compounds of general formula (II), wherein m, n and $R^1$ to $R^7$ are as hereinbefore defined, with carbon disulphide and subsequently with an alkylating agent of general formula

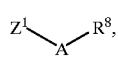

(IV)

wherein
A and $R^8$ are as hereinbefore defined, with the proviso that $R^8$ does not represent an optionally substituted phenyl or naphthyl group if A denotes a single bond, and $Z^1$ denotes a leaving group, e.g. a halogen atom, such as the chlorine, bromine or iodine atom, an alkylsulfonyloxy group with 1 to 10 carbon atoms in the alkyl moiety, a phenylsulphonyloxy or naphthylsuphonyloxy group optionally mono-, di- or trisubstituted by chlorine or bromine atoms, by methyl or nitro groups, whilst the substituents may be identical or different, and, if necessary, subsequently cleaving any protecting groups.

If $R^2$ denotes a hydrogen atom, first of all, conveniently, a compound of general formula (II), wherein $R^2$ denotes a protecting group, e.g. a tert. butoxycarbonyl group, is reacted and then the protecting group is cleaved by conventional methods, e.g. using trifluoroacetic acid or hydrogen chloride in dioxane.

If $R^2$ denotes an alkyl group substituted by a hydroxy group, it is advisable to protect the hydroxy group from the reaction e.g. by means of the tetrahydropyranyl group which is cleaved again after the reaction, e.g. using trifluoroacetic acid or hydrogen chloride in dioxane.

The reaction is appropriately carried out by first converting a compound of general formula (II) into the lithium salt in a suitable solvent, e.g. in tetrahydrofuran, e.g. using n-butyl-lithium at a temperature of from −20 to −10° C., and then reacting it with carbon disulphide. Then a compound of general formula (IV) is added in a suitable solvent, e.g. in tetrahydrofuran, dimethylformamide or a mixture of the two solvents and the reaction is carried out at 20–60° C.

In the reactions described hereinbefore, any reactive groups present such as hydroxy, carboxy, amino or alkylamino groups may be protected during the reaction by conventional protecting groups which are cleaved again after the reaction.

For example, a protecting group for a hydroxy group may be a trimethylsilyl, acetyl, benzoyl, tert.butyl, trityl, benzyl or tetrahydropyranyl group, and protecting groups for an amino or alkylamino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxan/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium (IV) ammonium nitrate in a solvent such as methylene chloride, acetonitrile or acetonitrile/water at temperatures of between 0 and 50° C., but preferably at ambient temperature.

A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid optionally using a solvent such as methylene chloride, dioxan or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

The compounds of general formula I prepared by the above methods can be purified and isolated by methods known per se, e.g. by crystallisation, distillation or chromatography.

Moreover, the compounds of general formula I obtained may optionally be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

In the compounds of general formula I according to the invention the aryl group bound to the cycloalkyl ring and the nitrogen atom may assume either an equatorial or axial arrangement. The invention thus includes both the pure isomers and the mixtures of the various isomers.

The starting compounds of general formula II are known and may be prepared using the methods described in DE-A-4 438 020 and EP-A-0 599 203.

Another method of preparing compounds of general formula II wherein $R^3$ to $R^5$ denote hydrogen atoms and the phenyl group is 1,4-disubstituted comprises converting a compound of general formula V

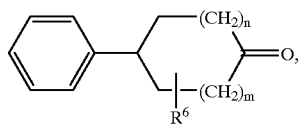

(V)

wherein m, n and $R^6$ are as hereinbefore defined, into a compound of formula VI

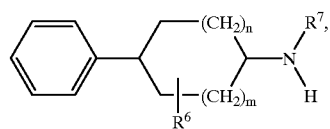

(VI)

using the methods described in DE-A-4 438 020 and EP-A-0 599 203, and then converting it by chloromethylation, preferably after introducing a protecting group at the nitrogen atom, e.g. a trifluoroacetyl group or 2,2,2-trichloroethoxycarbonyl group, into a compound of formula (VII)

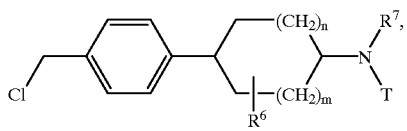

(VII)

wherein m, n and $R^7$ are as hereinbefore defined and T denotes a protecting group, e.g. the 2,2,2-trichloroethoxycarbonyl or trifluoroacetyl group, and finally reacting the compound of formula (VII) with an amine of formula H—$NR^1R^2$, wherein $R^1$ and $R^2$ are as hereinbefore defined and, after cleaving the protecting group, converting said compound into a compound of formula II by known methods.

The compounds of general formula I have valuable biological properties. They are inhibitors of cholesterol biosynthesis, particularly inhibitors of the enzyme 2,3-epoxysqualene-lanosterol-cyclase. In view of their biological properties they are suitable for treating diseases in which cholesterol biosynthesis is implicated, particularly for the treatment and prophylaxis of hypercholesterolaemia, hyperlipoproteinaemia and hypertriglyceridaemia and the resultant atheroscleotic vascular changes with their sequelae such as coronary heart disease, cerebral ischaemia, Claudicatio intermittens, gangrene et al.

For treating these diseases the compounds of general formula I may be used either on their own for monotherapy or in conjunction with other cholesterol- or lipid-lowering substances, whilst the compounds may preferably be administered as an oral preparation, and optionally also in the form of suppositories as a rectal formulation. The following are possible combination partners:

bile acid-binding resins such as cholestyramine, cholestipol and others, compounds which inhibit cholesterol absorption such as e.g. sitosterol and neomycin, compounds which interfere with cholesterol biosynthesis by a mechanism other than inhibition of 2,3-epoxysqualene-lanosterol-cyclase such as e.g. HMG-CoA-reductase inhibitors such as lovastatin, simvastatin, pravastatin, fluvastatin, atorvastatin, cerivastatin and others, squalene-epoxidase inhibitors such as NB 598 and analogous compounds and squalene-synthetase inhibitors such as compounds from the class of the isoprenoid-(phosphinylmethyl) phosphonates and squalestatin.

Other possible combination partners still to be mentioned are the fibrates, such as clofibrate, bezafibrate, gemfibrozil and others, nicotinic acid, the derivatives and analogues thereof such as acipimox, and probucol.

Furthermore the compounds of general formula I are suitable for the treatment of diseases connected with excessive cell proliferation. Cholesterol is an essential ingredient of cells and must be present in sufficient quantities for cell proliferation, i.e. cell division. The inhibition of cell proliferation by inhibiting cholesterol biosynthesis is described with reference to the smooth muscle cells with the HMG-CoA-reductase inhibitor of the mevinolin type lovastatin, as mentioned hereinbefore.

Examples of diseases connected with excessive cell proliferation are primarily tumour diseases. In cell culture and in-vivo experiments it has been shown that the lowering of the serum cholesterol or intervention in cholesterol biosynthesis by means of HMG-CoA-reductase inhibitors reduces tumour growth (Lancet 339, 1154–1156 [1992]). The compounds of formula I according to the invention are therefore potentially suitable for treating tumour diseases on the basis of their inhibitory effect on cholesterol biosynthesis. They may be used on their own or in support of known therapeutic principles.

Other examples are hyperproliferative skin diseases such as psoriasis, basal cell carcinomas, plate epithelial carcinomas, keratosis and keratinisation disorders. The term "psoriasis" used here denotes a hyperproliferatively inflammatory skin disease which changes the regulatory mechanism of the skin. In particular, lesions are formed which contain primary and secondary changes in the proliferation in the epidermis, inflammatory reactions of the skin and the expression of regulatory molecules such as lymphokines and inflammatory factors. Psoriatic skin is morphologically characterised by an increased turnover of epidermis cells, thickened epidermis, abnormal keratinisation of inflammatory cell infiltrates into the dermis layer and polymorphonuclear leukocyte infiltration into the epidermis, causing an increase in the basal cell cycle. Additionally, hyperkeratotic and parakeratotic cells are present. The terms "keratosis", "basal cell carcinomas", "plate epithelial carcinomas" and "keratinisation disorders" relate to hyperproliferative skin diseases in which the regulating mechanism for the proliferation and differentiation of the skin cells has been disrupted.

The compounds of formula I are effective as antagonists of skin hyperproliferation, i.e. as agents which inhibit the hyperproliferation of human keratinocytes. The compounds are consequently suitable as agents for treating hyperproliferative skin diseases such as psoriasis, basal cell carcinomas, keratinisation disorders and keratosis. For treating these diseases the compounds of formula I may be administered either orally or topically, and may be used either on their own in the form of monotherapy or in combination with known active substances.

Hyperproliferative vascular diseases such as stenoses and vascular occlusions based on the proliferation of smooth muscle cells and caused by surgical procedures such as PTCA (percutaneous transluminal coronary angioplasty) or bypass operations should also be mentioned. As mentioned hereinbefore this cell proliferation is known to be suppressed by HMG-CoA-reductase inhibitors of the mevinoline type, such as lovastatin. In view of their inhibitory activity on cholesterol biosynthesis the compounds of general formula I are also suitable for the treatment and prophylaxis of these diseases, and may be used either on their own or in conjunction with known active substances such as intravenously administered heparin, preferably by oral administration.

Another possible use of the compounds of general formula I according to the invention is the prophylaxis and treatment of gallstone problems. The formation of gallstones is triggered by the cholesterol concentration in the bile exceeding the maximum solubility of the cholesterol in the bile fluid, causing the cholesterol to be precipitated in the form of gallstones. Lipid-lowering substances from the fibrate class lead to increased precipitation of neutral steroids through the bile and increase the tendency to form gallstones.

By contrast, cholesterol biosynthesis inhibitors such as lovastatin or pravastatin do not result in increased gallstone formation; on the contrary they may bring about a reduction in the cholesterol concentration in the bile and hence lower the so-called lithogenic index, a measurement of the probability of gallstone formation. This is described in Gut 31, 348–350 [1990] and in Z. Gastroenterol. 29, 242–245 [1991].

Moreover, the efficacy of lovastatin in dissolving gallstones, particularly in conjunction with ursodeoxycholic acid, is described in Gastroenterology 102, No. 4, Pt. 2, A 319 [1992]. In view of their mode of activity the compounds of general formula I are therefore also important in the prevention and treatment of gallstone problems. They may be used either on their own or in conjunction with known therapies such as, for example, treatment with ursodeoxycholic acid or shockwave lithotripsy, and are preferably administered orally.

Finally, the compounds of general formula I are suitable for the treatment of infections caused by pathogenic fungi such as e.g. Candida albicans, Aspergillus niger, Trichophyton mentagrophytes, Penicillium sp., Cladosporium sp. and others. As mentioned earlier, the end product of sterol biosynthesis in the fungal organism is not cholesterol, but ergosterol which is essential for the integrity and function of the fungal cell membranes. Inhibiting ergosterol biosynthesis therefore leads to growth disorders and possibly the death of the fungal organisms.

For treating mycoses the compounds of general formula I may be administered either orally or topically. They may be used either on their own or in conjunction with known antimycotic active substances, particularly with those which interfere in other stages of sterol biosynthesis, such as for example the squalene-epoxidase inhibitors terbinafine and naftifine or the lanosterol-14α-demethylase inhibitors of the azole type such as ketoconazole and fluconazole.

Another possible use of the compounds of general formula I is their application in poultry rearing. Lowering the cholesterol content of eggs by administering the HMG-CoA-reductase inhibitor lovastatin to laying hens has been described (FASEB Journal 4, A 533, Abstracts 1543 [1990]). The production of low-cholesterol eggs is of interest as the cholesterol loading of the body can be reduced without changing eating habits by means of eggs with a reduced cholesterol content. In view of their inhibitory activity on cholesterol biosynthesis the compounds of general formula I can also be used in poultry rearing to produce low-cholesterol eggs, the substances preferably being given to the hens as a feed additive.

The biological activity of compounds of general formula I was determined by the following methods:

I. Measuring the Inhibition of $^{14}$C-acetate Incorporation Into the Steroids which can be Precipitated with Digitonin The inhibitory effect was investigated using the method described in J. Lipid. Res. 37, 148–157 [1996] at test concentrations of $10^{-8}$ and $10^{-9}$ mol/l.

By way of example, the test results for the following compounds (A) to (R) of general formula I and the comparison substances (U), (V) and (W) at these test concentrations are given:

(A) trans-S-(4-chlorophenyl)-N-4-[4-(dimethylaminomethyl)-phenyl]cyclohexyl-N-methyldithiocarbamate,
(B) trans-S-(3-fluorobenzyl)-N-4-[4-(dimethylaminomethyl)-phenyl]cyclohexyl-N-methyldithiocarbamate-hydrochloride,
(C) trans-S-(4-fluorobenzyl)-N-4-[4-(dimethylaminomethyl)-phenyl]cyclohexyl-N-methyldithiocarbamate-hydrochloride,
(D) trans-S-(4-chlorobenzyl)-N-4-[4-(dimethylaminomethyl)-phenyl]cyclohexyl-N-methyldithiocarbamate-hydrochloride,
(E) trans-O-(4-chlorophenyl)-N-4-[4-(dimethylaminomethyl)-phenyl]cyclohexyl-N-methylcarbamate-hydrochloride,
(F) cis-S-benzyl-N-4-[4-(dimethylaminomethyl)phenyl]-cyclohexyl-N-methyldithiocarbamate-hydrochloride,
(G) trans-O-(4-chlorophenyl)-N-4-[4-(dimethylaminomethyl)-phenyl]cyclohexyl-N-methylthiocarbamate-hydrochloride,
(H) trans-S-(4-chlorophenyl)-N-4-[4-(dimethylaminomethyl)-phenyl]cyclohexyl-N-methylthiocarbamate-hydrochloride,
(I) trans-O-(4-chlorophenyl)-N-methyl-N-4-[4-(piperidino-methyl)phenyl]cyclohexylcarbamate-hydrochloride,
(K) trans-O-(4-chlorophenyl)-N-methyl-N-4-[4-(pyrrolidino-methyl)phenyl]cyclohexylcarbamate-hydrochloride,
(L) trans-O-(4-chlorophenyl)-N-4-[4-(diethylaminomethyl)-phenyl]cyclohexyl-N-methylcarbamate-hydrochloride,
(M) trans-O-(4-chlorophenyl)-N-methyl-N-4-[4-(N-methyl-N-allylaminomethyl)phenyl]cyclohexylcarbamate,
(N) trans-O-(4-chlorophenyl)-N-methyl-N-4-[4-(N-methyl-N-propargylaminomethyl)phenyl]cyclohexylcarbamate,
(O) trans-N-4-[4-(dimethylaminomethyl)phenyl]cyclohexyl-N-methyl-O-(4-methylphenyl)carbamate-hydrochloride,
(P) trans-N-4-[4-(dimethylaminomethyl)phenyl]cyclohexyl-N-methyl-O-(4-methylphenyl)thiocarbamate-hydrochloride,
(Q) trans-N-Methyl-O-(4-methylphenyl)-N-4-[4-(piperidino-methyl)phenyl]cyclohexylthiocarbamate-hydrochloride,
(R) trans-N-4-[4-(dimethylaminomethyl)phenyl]cyclohexyl-O-(4-fluorophenyl)-N-methylcarbamate-hydrochloride,
(U) 1-(4-chlorobenzoyl)-4-[4-(2-oxazolin-2-yl)-benzylidene]-piperidine (EP-A-0 596 326, p. 16, compound A therein; J. Lipid. Res. 38, 564–575 [1997]),
(V) trans-N-(4-chlorobenzoyl)-N-methyl-[4-(4-dimethylamino)-methyl)phenyl]cyclohexylamine (DE-A-44 38 020; J. Lipid. Res. 37, 148–157 [1996]) and
(W) trans-O-(p-tolylacetyl)-4-(4-dimethylaminomethylphenyl)-cyclohexanol (WO 95/29148, p. 28, compound I therein).

The percentages by which the above compounds inhibit the $^{14}$C-acetate incorporation are shown in Table 1.

TABLE 1

| compound | $10^{-8}$ mol/l | $10^{-9}$ mol/l |
|---|---|---|
| (A) | −85 | −39 |
| (B) | −85 | −59 |
| (C) | −87 | −52 |
| (D) | −85 | −51 |
| (E) | −85 | −57 |
| (F) | −83 | −40 |
| (G) | −85 | −43 |
| (H) | −87 | −65 |
| (I) | −83 | −43 |
| (K) | −81 | −53 |
| (L) | −83 | −53 |
| (M) | −93 | −74 |
| (N) | −90 | −75 |
| (O) | −83 | −57 |
| (P) | −83 | −60 |
| (Q) | −79 | −51 |
| (R) | −86 | −63 |
| (U) | −54 | −07 |
| (V) | −59 | −23 |
| (W) | −72 | −21 |

The $IC_{50}$ values of compounds E, G, H, O and R were determined. These are given together with the $IC_{50}$ values of compounds U, V and W in Table 2.

TABLE 2

| compound | $IC_{50}$ (nmol/l) |
|---|---|
| (E) | 0.3 |
| (G) | 0.4 |
| (H) | 0.5 |
| (O) | 0.8 |
| (R) | 0.5 |
| (U) | 5.5 |
| (V) | 3.8 |
| (W) | 9.6 |

Table 2 shows that the compounds according to the invention are significantly superior to the comparison substances described earlier.

II. Measuring the in-vivo Activity in the Rat After Oral Administration

Inhibiting the enzyme 2,3-epoxysqualene-lanosterol-cyclase causes an increase in the 2,3-epoxisqualene levels in the liver and plasma. The quantity of 2,3-epoxysqualene formed therefore serves as a direct measurement of the potency on the animal as a whole. The amounts were determined using the method described in J. Lipid. Res. 38, 564–575, [1997] at t=3 or 8 hours after administration of the substance in concentrations of c=0.01, 0.03, 0.1, 0.3 and 1.0 mg/kg. Table 3 which follows gives the results obtained for the abovementioned substances A, B, C, E, G, H, O and R by way of example.

TAB. 3

| C [mg/kg] | 0.01 | | 0.03 | | 0.1 | | 0.3 | | 1.0 | |
|---|---|---|---|---|---|---|---|---|---|---|
| T [h] | 3 | 8 | 3 | 8 | 3 | 8 | 3 | 8 | 3 | 8 |
| A | 0.0 | 14.6 | 11.8 | 66.0 | 62.6 | 312.5 | | | 136.5 | 291.9 |
| B | | | 24.5 | 57.1 | 96.0 | 150.9 | 98.5 | 234.5 | | |
| C | 0.0 | 84.8 | 33.1 | 57.8 | 47.0 | 133.1 | 77.8 | 196.5 | 68.1 | 243.9 |
| E | 20.3 | 32.7 | 39.0 | 44.6 | 92.5 | 191.5 | 63.4 | 180.0 | | |
| G | 5.2 | 30.1 | 12.8 | 42.3 | 66.2 | 115.3 | 57.5 | 225.5 | | |
| H | 2.9 | 31.3 | 25.7 | 25.3 | 117.7 | 202.3 | 70.3 | 112.6 | | |
| O | | | | | 53.4 | 94.3 | 72.6 | 113.2 | 117.9 | 224.8 |
| R | 5.1 | 25.6 | 38.2 | 67.2 | 53.8 | 152.9 | 79.7 | 191.0 | 106.2 | 340.0 |

2,3-epoxysqualene concentration [μg/g] In the liver (rat)

In the control animals there were no measurable 2,3-epoxisqualene levels under these conditions.

III. Lipid Reduction in the Normolipaemic Golden Hamster

This was determined using the method described in J. Lipid. Res. 38, 564–575, (1997). At the end of the experiment the total cholesterol, β-lipoprotein-cholesterol and HDL-cholesterol were determined and compared with the values of a control group which were fed without any test substance.

The lipid-lowering activity of the abovementioned compounds E, G and I was tested.

The results are shown in Table 4.

TABLE 4

| Comp. | Dose [mg/kg/day] | Total cholesterol [%] | β-Lipoprotein-cholesterol [%] | HDL-cholesterol [%] |
|---|---|---|---|---|
| E | 0.5 | −22.5 | −27.5 | −18.2 |
| | 1.5 | −34.1 | −48.4 | −24.0 |
| | 4.9 | −34.3 | −45.1 | −25.1 |
| G | 0.5 | −27.7 | −40.2 | −21.1 |
| | 1.5 | −31.1 | −42.2 | −26.5 |
| | 4.9 | −26.5 | −33.2 | −24.3 |
| I | 0.46 | −16.1 | −26.2 | −3.3 |
| | 1.34 | −20.2 | −33.7 | −5.0 |
| | 4.89 | −25.7 | −36.1 | −16.2 |
| O | 5.87 | −17.3 | −22.5 | −12.7 |
| R | 1.73 | −16.5 | −14.3 | −19.7 |
| | 6.37 | −27.8 | −34.3 | −20.0 |

Under these conditions the compounds exhibited no toxic effects.

IV. Inhibition of Cell Proliferation

HaCat cells (human keratinocytes) are seeded at a density of 10,000 cells per well in a 96 well microtitre plate. The culture medium used is Dulbecco's modified eagle medium (DMEM) with the addition of 10% calf serum. The cells are incubated for two days in an incubator, then the test substance, dissolved in dimethyl sulphoxide and diluted with culture medium, is added. After another two days incubation, 5-bromo-2'-deoxyuridine is added and the test results are determined according to the instructions (Boehringer Mannheim, Cell proliferation ELISA, BrdU (colorimetric)). The BrdU measurement was carried out at 380–490 nm in the Plate Reader made by Bio Rad.

The proliferation-inhibiting activity of compounds E, G and H was investigated. The average of three measurements was calculated and the results are given as a percentage of the control (Table 5).

TABLE 5

| Test substance ($10^{-6}$ mol/l) | Inhibitory effect |
|---|---|
| control | 100% |
| E | 19.6 |
| G | −2.8 |
| H | −8.6 |

V. Determining the Fungistatic Activity

The fungistatic activity was determined by the series dilution test (microtitre system). Sabouraud broth was used as the nutrient medium. The inoculum amounted to about $10^4$ to $10^5$ CFU/ml (CFU=colony-forming units); the incubation period was 2 to 4 days at 26° C.

The lowest concentration which allows no visible growth (minimum inhibitory concentration MIC) was determined.

The abovementioned compounds B, E, G, I, K, L, N, Q and R were tested. The results are assembled in the following Table 6. The MIC is given in μg/ml.

The following test pathogens were used:

| Test pathogen | Abbreviation |
|---|---|
| Cand. albicans ATCC 10231 | Cand. |
| Sacch. carlsbergensis ATCC 9080 | Sacc. |
| Rhod. rubra 49 | Rhod. |
| Asp. niger ATCC 16404 | Asp. |
| Trich. mentagrophytes ATCC 9129 | Trich. |
| Pen. notatum CBS 19746 | Pen. |

TABLE 6

| Test comp. | MIC [μg/ml] | | | | | |
|---|---|---|---|---|---|---|
| | Cand. | Sacc. | Rhod. | Asp. | Trich. | Pen. |
| B | 2 | 8 | 2 | 2 | 1 | 2 |
| E | 16 | 128 | 16 | 4 | 2 | 2 |
| G | 4 | 32 | 8 | 4 | 1 | 1 |
| I | 64 | 64 | 64 | 256 | 8 | 64 |
| K | 64 | 128 | 32 | 16 | 2 | 8 |
| L | 32 | 128 | 8 | 32 | 1 | 64 |
| N | 8 | 64 | 16 | >512 | 8 | 8 |
| Q | 16 | 32 | 8 | 128 | 2 | 64 |
| R | 64 | 512 | 16 | 16 | 2 | 16 |

For pharmaceutical use the compounds of general formula I may be incorporated in the conventional pharmaceutical preparations for oral, rectal and topical administration in a manner known per se.

Formulations for oral administration include for example plain and coated tablets and capsules. For rectal administration suppositories may be used. The daily dose is between 0.1 and 200 mg for a person with a body weight of 60 kg, but the preferred daily dose is from 1 to 100 mg for a person weighing 60 kg. The daily dose is preferably divided into 1 to 3 individual doses.

For topical application the compounds may be administered in preparations containing about 1 to 1000 mg, particularly 10 to 300 mg of active substance per day. The daily dose is preferably divided into 1 to 3 individual doses.

Topical formulations include gels, creams, lotions, ointments, powders, aerosols and other conventional formulations for applying medicaments to the skin. The amount of active substance for topical use is 1 to 50 mg per gram of formulation, but preferably 5 to 20 mg per gram of formulation. Apart from application to the skin the topical formulations of the present invention may also be used in the treatment of mucous membranes accessible to topical treatment. For example, the topical formulations may be applied to the mucous membranes of the mouth, lower colon, etc.

For use in poultry rearing for the production of low-cholesterol eggs the active substances of general formula I are administered to the anmals by the usual methods as an additive to suitable feedstuffs. The concentration of the active substances in the finished feed is normally 0.01 to 1%, but preferably 0.05 to 0.5%.

The active substances may be added to the feed as they are. Thus, the feeds for laying hens according to the invention contain, in addition to the active substance and optionally a conventional vitamin-mineral mixture, maize, soya bean flour, meat meal, edible fat and soya oil, for example. To this feed is added one of the abovementioned compounds of formula I as active substance in a concentration of from 0.01 to 1%, but preferably 0.05 to 0.5%.

The following Examples serve to illustrate the invention more fully. The $R_f$-values given were determined on ready-made plates obtained from E. Merck of Darmstadt on:

a) aluminium oxide F-254 (type E)
b) silica gel 60 F-254
Examples of the preparation of the starting materials:

EXAMPLE A trans-N-Methyl-4-[4-(piperidinomethyl)phenyl] cyclohexylamine 26 g (0.15 mol) of 4-phenylcyclohexanone are stirred with 160 ml of a 6 % methylamine solution in toluene in the presence of 30 g of molecular sieve M 3 Å overnight in a sealed flask. After filtering and concentration by evaporation the residue is dissolved in 200 ml of methanol and at −20° C. 7.8 g sodium borohydride are added batchwise. After it has all been added the mixture is stirred overnight at ambient temperature. After evaporation of the methanol the remainder is taken up in 150 ml of ice water and made strongly acidic with conc. hydrochloric acid. After saturation with common salt the hydrochloride precipitated is suction filtered, the mother liquor is made strongly alkaline with 6N sodium hydroxide solution, extracted with ethyl acetate, dried and evaporated down. The hydrochloride precipitated is suspended in a mixture of water and ethyl acetate and, under cooling, made strongly alkaline with 6N sodium hydroxide solution. The ethyl acetate phase is washed with water and saturated saline solution, dried and evaporated down. Crystallisation of the residue from petroleum ether yields 15.1 g trans-N-methyl-4-phenylcyclohexylamine (colourless crystals). The petroleum ether mother liquor is evaporated down and combined with the evaporation residue from the hydrochloride precipitation. Separation on aluminium oxide (activity stage III, ethyl acetate/petroleum ether=1:1 to 2:1, v:v) yields 2.4 g cis-N-methyl-4-phenylcyclohexylamine, 4.4 g trans compound and 5.1 g of a mixture of cis- and trans-N-methyl-4-phenylcyclohexylamine. Total yield of trans-N-methyl-4-phenylcyclohexylamine: 19.5 g (68.6 % of theory), colourless crystals.

19.5 g (0.103 mol) of trans-N-methyl-4-phenylcyclohexylamine and 12.1 g (0.12 mol) of triethylamine are dissolved in 200 ml of ethyl acetate. Whilst cooling with ice 24.0 g (0.113 mol) of 2,2,2-trichloroethyl chloroformate in 50 ml ethyl acetate are added dropwise and stirred for a further 2 hours. After standing overnight at ambient temperature the mixture is diluted with ethyl acetate and washed with water, dilute hydrochloric acid, again with water and finally with saturated saline solution. The residue obtained after drying (magnesium sulphate) and evaporation is dissolved under heating in a mixture of petroleum ether and ethyl acetate (10:1, v:v). Slow cooling, ultimately to 0° C., yields 34.3 g (91.3% of theory) of trans-N-methyl-N-2,2,2-trichloro-ethoxycarbonyl-4-phenylcyclohexylamine as colourless crystals, melting point 84–86° C.

A further 1.1 g (2.9 % of theory) of this product are obtained after evaporation of the mother liquor and purification of the residue on silica gel (petroleum ether/ethyl acetate=10:1 to 5:1, v:v).

35.4 g (0.097 mol) of this compound are dissolved in 950 ml of dichloromethane. After the addition of 30.7 g (0.345 mol) of paraformaldehyde and 30.7 g (0.226 mol) of zinc chloride, hydrogen chloride is introduced (2 hours at ambient temperature) and stirred overnight at ambient temperature. Excess hydrogen chloride is eliminated in a nitrogen current and the reaction mixture is poured into cooled aqueous disodium hydrogen phosphate solution. The organic phase is separated off, the aqueous phase is extracted twice with methylene chloride, the organic phases are combined, washed with water, dried with magnesium sulphate and evaporated down. The residue is purified by chromatography on silica gel (petroleum ether/ethyl acetate=20:1 to 15:1, v:v). In addition to 14.0 g (39.5 % of theory) of unchanged starting material, 19.0 g (47.4 % of theory) of trans-4-(4-chloromethylphenyl)-N-methyl-N-2,2,2-trichlorethoxycarbonyl-cyclohexylamine is obtained in the form of colourless crystals, Rf value 0.38 (silica gel, petroleum ether/ethyl acetate 10:1, v:v).

830 mg (2mmol) of this compound are dissolved in a mixture of 10 ml of tetrahydrofuran and ethanol, 510 mg (6 mmol) of piperidine are added, the mixture is stirred overnight at ambient temperature and then stirred for 3 hours at 50° C. After cooling it is poured onto water and extracted three times with ethyl acetate. The organic phase is washed with water and saturated saline solution, dried (magnesium sulphate) and evaporated down. Purification of the residue by chromatography (aluminium oxide, activity stage III, petroleum ether/ethyl acetate=10:1) yields 750 mg (81.2 % of theory) of trans-N-methyl-N-2,2,2-trichloroethoxycarbonyl-4-[4-(piperidinomethyl)phenyl] cyclohexylamine (pale yellow crystals), Rf value 0.52 (aluminium oxide, petroleum ether/ethyl acetate 5:1).

730 mg (1.58 mmol) of this compound are dissolved in 1 ml of glacial acetic acid and 5 ml water. At ambient temperature 1.5 g of zinc powder are added in one go (vigorous foaming after a short time). The mixture is stirred for 30 minutes at ambient temperature, then for 1 hour at 50° C., cooled, water and ethyl acetate are added and the resulting mixture is made strongly alkaline with 6N-sodium hydroxide solution. After filtration the organic phase is separated off, washed with water and saturated saline solution, dried (magnesium sulphate) and evaporated down. 340 mg (75.1 % of theory) of trans-N-methyl-4-[4-(piperidinomethyl)phenyl]cyclohexylamine are obtained (colourless crystals), Rf value 0.3 (aluminium oxide, methylene chloride/methanol 40:1, v:v).

The following are obtained analogously:
(1) trans-N-methyl-4-[4-(pyrrolidinomethyl)phenyl] cyclohexylamine, from 4-phenylcyclohexanone and pyrrolidine; colourless crystals; Rf value 0.44 (aluminium oxide, petroleum ether/ethyl acetate 5:1, v:v)
(2) trans-4-[4-(diethylaminomethyl)phenyl]-N-methylcyclohexylamine, from 4-phenylcyclohexanone and diethylamine; colourless solid; Rf value 0.25 (aluminium oxide, methylene chloride/methanol 40:1, v:v)
(3) trans-4-[4-[(2-hydroxyethyl)methylaminomethyl] phenyl]-N-methylcyclohexylamine, from 4-phenylcyclohexanone and N-methylethanolamine; colourless solid; Rf value 0.33 (aluminium oxide, methylene chloride/methanol 20:1, v:v)
(4) trans-4-[4-(di-n-hexylaminomethyl)phenyl]-N-methylcyclohexylamine, from 4-phenylcyclohexanone and di-n-hexylamine; colourless solid; Rf value 0.26 (aluminium oxide, methylene chloride/methanol 40:1, v:v)
(5) trans-4-[4-(di-sec-butylaminomethyl)phenyl]-N-methylcyclohexylamine, from 4-phenylcyclohexanone and di-sec-butylamine; colourless solid; Rf value 0.58 (aluminium oxide, methylene chloride/methanol 20:1, v:v)
(6) trans-N-methyl-4-[4-(N-methylallylaminomethyl) phenyl]cyclohexylamine, from 4-phenylcyclohexanone and N-methylallylamine;, colourless solid; Rf value 0.22 (aluminium oxide, methylene chloride/methanol 40:1, v:v)
(7) trans-N-methyl-4-[4-(N-methylpropargylaminomethyl) phenyl]cyclohexylamine, from 4-phenylcyclohexanone and N-methylpropargylamine; colourless crystals; Rf value 0.23 (aluminium oxide, methylene chloride/methanol 40:1, v:v
(8) cis/trans-N-methyl-4-[4-(morpholinomethyl)phenyl] cyclohexylamine, from 4-phenylcyclohexanone and morpholine; colourless solid; Rf values 0.26 and 0.48 (aluminium oxide, petroleum ether/ethyl acetate=5:1, v:v)

Examples of the preparation of the end products:

Example 1 trans-O-(4-chlorophenyl)-N-4-[4-(dimethylaminomethyl)phenyl]-cyclohexyl-N-methylcarbamate-hydrochloride 250 mg (1 mmol) of trans-4-[4-(dimethylaminomethyl) phenyl]-N-methylcyclohexylamine and 0.3 ml triethylamine are placed in 20 ml of methylene chloride and 210 mg (1.1 mmol) of 4-chlorophenyl chloroformate in a little methylene chloride are added dropwise. The mixture is stirred overnight, then diluted with methylene chloride, washed with water and saturated saline solution, dried and evaporated down. The residue is purified by column chromatography (silica gel, methylene chloride/methanol=9:1, v:v). The product obtained is dissolved in methylene chloride, mixed with ethereal hydrochloric acid and the hydrochloride is precipitated by the addition of ether. After washing with ether and drying, 276 mg (63.1% of theory) of the title compound are obtained as a colourless, amorphous powder.

Rf value of the free base: 0.62 (silica gel, methylene chloride/methanol=9:1, v:v)

$^1$H-NMR spectrum (200 MHz, DMSO-$d_6$), signals at ppm: 1.5–1.95 (m, 8H), 2.5–2.7 (s+m, 7H), 2.8–3.0 (2s, 3H), 3.9–4.1 (m, 1H), 4.2 (s, 2H), 7.1–7.5 (m, 8H)

The following are obtained analogously:
(1) trans-O-benzyl-N-4-[4-(dimethylaminomethyl)phenyl]-cyclohexyl-N-methylcarbamate, from trans-4-[4-(dimethylaminomethyl)phenyl]-N-methylcyclohexylamine and benzyl chloroformate; colourless oil (after purification by column chromatography on aluminium oxide (ethyl acetate/petroleum ether=3:1, v:v)); Rf value: 0.44 (aluminium oxide, ethyl acetate/petroleum ether=3:1)
(2) trans-O-cyclohexyl-N-4-[4-(dimethylaminomethyl) phenyl]-cyclohexyl-N-methylcarbamate, from trans-4-[4-(dimethylaminomethyl)phenyl]-N-methylcyclohexylamine and cyclohexyl chloroformate; melting point: 72° C. (after column chromatography on aluminium oxide (petroleum ether/ethyl acetate=3:1, v:v))
(3) trans-S-(4-chlorophenyl)-N-4-[4-(dimethylaminomethyl)phenyl]-cyclohexyl-N-methyldithiocarbamate, from trans-4-[4-(dimethylaminomethyl)phenyl]-N-methylcyclohexylamine and 4-chlorophenyl dithiochloroformate (prepared from 4-chlorothiophenol and thiophosgene); colourless powder (after column chromatography on silica gel (methylene chloride/methanol=9:1, v:v)); Rf value: 0.65 (silica gel, methylene chloride/methanol=5:1, v:v)
(4) cis-S-(4-chlorophenyl)-N-4-[4-(dimethylaminomethyl) phenyl]-cyclohexyl-N-methyldithiocarbamate-hydrochloride, from cis-4-[4-(dimethylaminomethyl) phenyl]-N-methylcyclohexylamine and 4-chlorophenyl dithiochloroformate; colourless powder; Rf value of the free base: 0.65 (silica gel, methylene chloride/methanol=5:1, v:v)
(5) trans-S-(4-chlorophenyl)-N-4-[4-(dimethylaminomethyl)phenyl]-cyclohexyl-N-methylthiocarbamate-hydrochloride, from trans-4-[4-(dimethylaminomethyl)phenyl]-N-methylcyclohexylamine and S-(4-chlorophenyl)-chlorothioformate; colourless powder; Rf value of the free base: 0.5 (silica gel, methylene chloride/methanol=9:1, v:v)
(6) cis/trans-O-(4-chlorophenyl)-N-methyl-N-4-[4-(morpholinomethyl)phenyl]cyclohexylcarbamate-hydrochloride, from cis/trans-N-methyl-N-4-[4-(morpholinomethyl)phenyl]cyclohexylamine and 4-chlorophenyl chloroformate; colourless powder; Rf value of the free base: 0.35 (aluminium oxide, petroleum ether/ethyl acetate=5:1, v:v)

(7) trans-O-(4-chlorophenyl)-N-methyl-N-4-[4-(piperidino-methyl)phenyl]cyclohexylcarbamate-hydrochloride, from trans-N-methyl-N-4-[4-(piperidinomethyl)phenyl]cyclohexylamine and 4-chlorophenyl chloroformate; colourless powder; Rf value of the free base: 0.48 (aluminium oxide, petroleum ether/ethyl acetate=10:1, v:v)

(8) trans-O-(4-chlorophenyl)-N-methyl-N-4-[4-(pyrrolidino-methyl)phenyl]cyclohexylcarbamate-hydrochloride, from trans-N-methyl-N-4-[4-(pyrrolidinomethyl)phenyl]cyclohexylamine and 4-chlorophenyl chloroformate; colourless powder; Rf value of the free base: 0.32 (aluminium oxide, petroleum ether/ethyl acetate=5:1, v:v)

(9) trans-O-(4-chlorophenyl)-N-4-[4-(diethylaminomethyl) phenyl]cyclohexyl-N-methylcarbamate-hydrochloride, from trans-N-4-[4-(diethylaminomethyl)phenyl]-N-methylcyclohexylamine and 4-chlorophenyl chloroformate; colourless powder; Rf value of the free base: 0.48 (aluminium oxide, petroleum ether/ethyl acetate=5:1, v:v)

(10) trans-O-(4-chlorophenyl)-N-4-[4-[(2-hydroxyethyl)-methylaminomethyl]phenyl]cyclohexyl-N-methylcarbamate-hydrochloride, from trans-N-4-[4-[(2-hydroxyethyl)methylaminomethyl]phenyl]-N-methylcyclohexylamine and 4-chlorophenyl chloroformate; colourless powder; Rf value of the free base: 0.19 (aluminium oxide, petroleum ether/ethyl acetate=1:1, v:v)

(11) trans-(O-4-chlorophenyl)-N-4-[4-(di-n-hexylaminomethyl)-phenyl]cyclohexyl-N-methylcarbamate-hydrochloride, from trans-N-4-[4-(di-n-hexylaminomethyl)phenyl]-N-methylcyclohexylamine and 4-chlorophenyl chloroformate; colourless powder; Rf value of the free base: 0.58 (aluminium oxide, petroleum ether/ethyl acetate=10:1, v:v)

(12) trans-N-4-[4-(di-sec-butylaminomethyl)phenyl]cyclohexyl-O-(4-chlorophenyl)-N-methylcarbamate-hydrochloride, from trans-N-4-[4-(di-sec-butylaminomethyl)phenyl]-N-methylcyclohexylamine and 4-chlorophenyl chloroformate; colourless powder; Rf value of the free base: 0.60 (aluminium oxide, petroleum ether/ethyl acetate=10:1, v:v)

(13) trans-O-(4-chlorophenyl)-N-methyl-N-4-[4-(N-methyl-N-allylaminomethyl)phenyl]cyclohexylcarbamate, from trans-N-methyl-N-4-[4-(N-methyl-N-allylaminomethyl)phenyl]cyclohexylamine and 4-chlorophenyl chloroformate; colourless powder; Rf value: 0.58 (petroleum ether/ethyl acetate=5:1, v:v)

(14) trans-O-(4-chlorophenyl)-N-methyl-N-4-[4-(N-methyl-N-propargylaminomethyl)phenyl]cyclohexylcarbamate, from trans-N-methyl-N-4-[4-(N-methyl-N-propargylaminomethyl)phenyl]cyclohexylamine and 4-chlorophenyl chloroformate; colourless powder; Rf value: 0.38 (aluminium oxide, petroleum ether/ethyl acetate=5:1, v:v)

(15) trans-O-(4-chlorophenyl)-N-methyl-N-4-[4-(methylaminomethyl)phenyl]cyclohexylcarbamate-hydrochloride, from trans-N-4-[4-(tert.-butyloxycarbonylmethylaminomethyl)-phenyl]-N-methylcyclohexylamine and 4-chlorophenyl chloroformate, followed by cleaving of the tert.butyloxycarbonyl group with ethereal hydrochloric acid; colourless powder; Rf value of the free base: 0.5 (aluminium oxide, methylene chloride/methanol=40:1, v:v)

(16) trans-N-4-[4-(dimethylaminomethyl)phenyl]cyclohexyl-N-methyl-O-(4-methylphenyl)carbamate, from N-4-[4-(dimethylaminomethyl)phenyl]-N-methylcyclohexylamine and 4-methylphenyl chloroformate; Rf value of the free base: 0.47 (aluminium oxide, petroleum ether/ethyl acetate=5:1, v:v); melting point of the free base: 93° C.

By treating with hydrochloric acid the hydrochloride was obtained; colourless powder, melting point 260° C.

By treating the free base with methanesulphonic acid in an ethyl acetate-ether mixture the methanesulphonate was obtained. Colourless powder, melting point 165° C.

By treating the free base with L-tartaric acid in a methanol-ethyl acetate mixture the tartrate was obtained. Colourless powder, melting point 135° C.

(17) trans-N-methyl-O-(4-methylphenyl)-N-4-[4-(piperidino-methyl)phenyl]cyclohexylthiocarbamate-hydrochloride, from trans-N-methyl-N-4-[4-(piperidinomethyl)phenyl]cyclohexylamine and O-4-methylphenyl chlorothioformate; colourless powder; Rf value of the free base: 0.35 (aluminium oxide, petroleum ether/ethyl acetate=10:1, v:v)

(18) trans-N-methyl-O-(4-methylphenyl)-N-4-[4-(piperidino-methyl)phenyl]cyclohexylcarbamate-hydrochloride, from trans-N-methyl-N-4-[4-(piperidinomethyl)phenyl]-cyclohexylamine and 4-methylphenyl chloroformate; colourless powder; Rf value of the free base: 0.43 (aluminium oxide, petroleum ether/ethyl acetate=10:1, v:v)

(19) trans-N-4-[4-(dimethylaminomethyl)phenyl]cyclohexyl-N-methyl-O-(4-methylphenyl)thiocarbamate-hydrochloride, from trans-N-4-[4-(dimethylaminomethyl)phenyl]-N-methylcyclohexylamine and O-4-methylphenyl chlorothioformate; colourless powder; Rf value of the free base: 0.29 (aluminium oxide, petroleum ether/ethyl acetate=5:1, v:v)

(20) trans-N-4-[4-(dimethylaminomethyl)phenyl] cyclohexyl-O-4-fluorophenyl-N-methylcarbamate, from trans N-4-[4-(dimethylaminomethyl)phenyl]-N-methylcyclohexylamine and O-4-fluorophenyl chloroformate; Rf value of the free base: 0.34 (aluminium oxide, petroleum ether/ethyl acetate=5:1, v:v); melting point of the free base 85° C.

By treating with hydrochloric acid the hydrochloride was obtained; colourless powder, melting point 250° C.

By treating the free base with methanesulphonic acid in an ethyl acetate-ether mixture the methanesulphonate was obtained. Colourless powder, melting point 190° C.

By treating the free base with L-tartaric acid in a methanol-ethyl acetate mixture the tartrate was obtained. Colourless powder, melting point 165° C.

(21) trans-O-(4-Fluorophenyl)-N-methyl-N-4-[4-(piperidino-methyl)phenyl]cyclohexylcarbamate-hydrochloride, from N-methyl-N-4-[4-(piperidinomethyl)phenyl]cyclohexylamine and 4-fluorophenyl chloroformate; colourless powder; Rf value of the free base: 0.49 (aluminium oxide, petroleum ether/ethyl acetate=5:1, v:v)

(22) trans-N-methyl-O-phenyl-N-4-[4-(piperidinomethyl)phenyl]cyclohexylcarbamate-hydrochloride, from trans N-methyl-N-4-[4-(piperidinomethyl)phenyl]cyclohexylamine and phenyl chloroformate; colourless powder; melting point: 218–223° C.

Example 2 trans-O-(4-chlorophenyl)-N-4-[4-(dimethylaminomethyl)phenyl]-cyclohexyl-N-methylthiocarbamate-hydrochloride A solution of 8.6 g (35 mmol) of trans-4-[4-(dimethylaminomethyl)phenyl]-N-methylcyclohexylamine in 100 ml of chloroform is combined with 35 ml of 1N-sodium hydroxide solution and 70 ml of water whilst cooling with ice. Whilst stirring vigorously, 7.4 g of O-4-chlorophenyl chlorothioformate in 50 ml of chloroform are added dropwise within 20 minutes, whilst cooling with ice, and stirred for 30 minutes at 0° C. and then for 1 hour at ambient temperature. The organic phase is separated off, washed with water, dried with magnesium sulphate and evaporated down. The product obtained after purification by column chromatography (silica gel, methylene chloride/methanol=5:1, v:v) is dissolved in 50 ml methylene chloride and mixed with ethereal hydrochloric acid and then ether. Yield: 11.3 g (71.2 % of theory) of the title compound; colourless powder; melting point: 257–259° C. (decomp.).

$^1$H-NMR spectrum (200 MHz, DMSO-$d_6$); signals at ppm: 1.5–2.0 (m, 8 H), 2.55–2.7 (s+m, 6+1H), 3.3–3.4 (d, 3H), 4.2 (s, 2H), 4.6 and 4.9 (2m, 1H), 7.1–7.5 (m, 8H)

Example 3 trans-S-benzyl-N-4-[4-(dimethylaminomethyl) phenyl]cyclohexyl-N-methyldithiocarbamate To 500 mg (2mmol) of trans-N-4-[4-(dimethylaminomethyl)-phenyl]-N-methylcyclohexylamine, dissolved in 12 ml of tetrahydrofuran, are added dropwise, at −15 to −10° C, 1.25 ml of a 6-molar solution of n-butyllithium in n-hexane. The mixture is stirred for 1 hour at −15° C. and then 182 mg (2.4 mmol) of carbon disulphide in 1 ml of tetrahydrofuran are added. After one hour at −10° C., 340 mg (2 mmol) of benzyl bromide in 2 ml of tetrahydrofuran are added dropwise at 0° C. and the mixture is then stirred overnight at ambient temperature. After the addition of water it is extracted with ether, the organic phase is dried with magnesium sulphate and evaporated down. After purification by column chromatography (aluminium oxide, petroleum ether/ethyl acetate=5:1, v:v) 280 mg (33.9% of theory) of the title compound are obtained in the form of colourless crystals.

Rf value: 0.46 (aluminium oxide, petroleum ether/ethyl acetate=5:1, v:v).

$^1$H-NMR spectrum (200 MHz,DMSO-$d_6$); signals at ppm: 1.4–2.0 (m, 8H), 2.1 (s, 6H), 2.5 (m, 1H), 3.2–3.4 (3s, 5H), 4.5+5.5 (2m, 1H), 4.5 (s, 2H), 7.2–7.5 (m, 9H)

The following are obtained analogously:
(1) trans-S-cyclohexylmethyl-N-4-[4-(dimethylaminomethyl)-phenyl]cyclohexyl-N-methyldithiocarbamate, from trans-N-4-[4-(dimethylaminomethyl)phenyl]-N-methylcyclohexylamine and (bromomethyl)-cyclohexane; colourless crystals; Rf value: 0.5 (aluminium oxide, petroleum ether/ethyl acetate=5:1, v:v)
(2) trans-S-cyclohexyl-N-4-[4-(dimethylaminomethyl) phenyl]-cyclohexyl-N-methyldithiocarbamate, from trans-N-4-[4-(dimethylaminomethyl)phenyl]-N-methylcyclohexylamine and cyclohexylbromide; colourless crystals; Rf value: 0.53 (aluminium oxide, petroleum ether/ethyl acetate=5:1, v:v)
(3) trans-S-(n-butyl)-N-4-[4-(dimethylaminomethyl) phenyl]-cyclohexyl-N-methyldithiocarbamate-hydrochloride, from trans-N-4-[4-(dimethylaminomethyl)phenyl]-N-methylcyclohexylamine and n-butylbromide; colourless powder; Rf value of the free base: 0.48 (aluminium oxide, petroleum ether/ethyl acetate=5:1)
(4) trans-N-4-[4-(dimethylaminomethyl)phenyl]cyclohexyl-S-(2-fluorobenzyl)-N-methyldithiocarbamate-hydrochloride, from trans-N-4-[4-(dimethylaminomethyl)phenyl]-N-methylcyclohexylamine and 2-fluorobenzylchloride; colourless powder; Rf value of the free base: 0.63 (silica gel, methylene chloride/methanol=5:1, v:v)
(5) trans-N-4-[4-(dimethylaminomethyl)phenyl]cyclohexyl-S-3-fluorobenzyl-N-methyldithiocarbamate-hydrochloride, from trans-N-4-[4-(dimethylaminomethyl)phenyl]-N-methylcyclohexylamine and 3-fluorobenzylchloride; colourless powder; Rf value of the free base: 0.57 (silica gel, methylene chloride/methanol=5:1, v:v)
(6) trans-N-4-[4-(dimethylaminomethyl)phenyl]cyclohexyl-S-(4-fluorobenzyl)-N-methyldithiocarbamate-hydrochloride, from trans-N-4-[4-(dimethylaminomethyl)phenyl]-N-methylcyclohexylamine and 4-fluorobenzylchloride; colourless powder; Rf value of the free base: 0.57 (silica gel, methylene chloride/methanol=5:1, v:v).
(7) trans-S-(4-chlorobenzyl)-N-4-[4-(dimethylaminomethyl)-phenyl]cyclohexyl-N-methyldithiocarbamate-hydrochloride, from trans-N-4-[4-(dimethylaminomethyl)phenyl]-N-methylcyclohexylamine and 4-chlorobenzylchloride; colourless powder; Rf value of the free base: 0.48 (silica gel, methylene chloride/methanol=5:1, v:v)
(8) trans-N-4-[4-(dimethylaminomethyl)phenyl]cyclohexyl-N-methyl-S-(1-phenethyl)dithiocarbamate-hydrochloride, from trans-N-4-[4-(dimethylaminomethyl)phenyl]-N-methylcyclohexylamine and 1-phenethylchloride; colourless powder; Rf value of the free base : 0.60 (silica gel, methylene chloride/methanol=5:1, v:v)
(9) cis-S-benzyl-N-4-[4-(dimethylaminomethyl)phenyl]-cyclohexyl-N-methyldithiocarbamate-hydrochloride, from cis-N-4-[4-(dimethylaminomethyl)phenyl]-N-methylcyclohexylamine and benzylbromide; colourless powder; Rf value of the free base: 0.51 (silica gel.methylene chloride/methanol=5:1, v:v)
(10) trans-S-benzyl-N-4-[4-(dimethylaminomethyl)phenyl]-cyclohexyl-N-isopropyldithiocarbamate-hydrochloride, from trans-N-4-[4-(dimethylaminomethyl)phenyl]-N-isopropyl-cyclohexylamine and benzylbromide; colourless powder; Rf value of the free base: 0.58 (silica gel, methylene chloride/methanol=5:1, v/v)
(11) trans-S-benzyl-N-4-[4-(dimethylaminomethyl)phenyl]-cyclohexyl-N-(n-hexyl)dithiocarbamate-hydrochloride, from trans-N-4-[4-(dimethylaminomethyl)phenyl]-N-(n-hexyl)-cyclohexylamine and benzyl bromide; colourless powder; Rf value of the free base: 0.63 (silica gel, methylene chloride/methanol=5:1, v:v).
(12) trans-N-allyl-S-benzyl-N-4-[4-(dimethylaminomethyl)-phenyl] cyclohexyldithiocarbamate-hydrochloride, from trans-N-allyl-N-4-[4-(dimethylaminomethyl)phenyl] cyclohexylamine and benzyl bromide; colourless powder; Rf value of the free base: 0.60 (silica gel, methylene chloride/methanol=5:1,v:v).

What is claimed is:
1. A compound of general formula I:

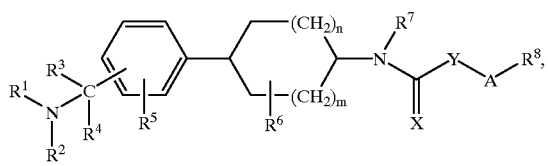

wherein:
m is 0 or 1;
n is 1 or 2;
A is a single bond, a straight-chained or branched $C_{1-8}$-alkylene group, a $C_{2-8}$-alkenylene or $C_{2-8}$-alkynylene group, wherein an unsaturated group is not directly bound to the group Y;
X is an oxygen or sulfur atom;
Y is an oxygen or sulfur atom;
$R^1$ is a straight-chained or branched $C_{1-8}$-alkyl group, a $C_{1-6}$-alkenyl group, or a $C_{1-6}$-alkynyl group, wherein the multiple bond is isolated from the nitrogen-carbon bond,
$R^2$ is a hydrogen atom, a straight-chained or branched $C_{1-8}$-alkyl group which is optionally substituted by a hydroxy or alkoxy group, a $C_{1-6}$-alkenyl group or a $C_{1-6}$-alkynyl group, wherein a hydroxy and alkoxy substituent is not bound in the 1-position and a multiple bond is isolated from the nitrogen-carbon bond, or
$R^1$ and $R^2$ together with the nitrogen atom are a 5- to 7-membered, saturated heterocyclic ring wherein a methylene group isolated from the nitrogen atom is optionally replaced by an oxygen or sulfur atom or by an —NH— or —N(alkyl)- group;
$R^3$ to $R^6$, which are identical or different, are hydrogen atoms or alkyl groups;
$R^7$ is a straight-chained or branched $C_{1-6}$-alkyl group, a $C_{1-6}$-alkenyl group or a $C_{1-6}$-alkynyl group, wherein the multiple bond is isolated from the nitrogen-carbon bond; and
$R^8$ is a $C_{3-7}$-cycloalkyl group, a phenyl or naphthyl group optionally substituted by one or two halogen atoms or by an alkyl, alkoxy, trifluoromethyl, or cyano group,
wherein, unless otherwise stated, alkyl groups contained in the groups mentioned above each contain 1 to 3 carbon atoms and a halogen atom mentioned above is a fluorine, chlorine, or bromine atom,
or a pharmaceutically acceptable salt thereof.
2. The compound of general formula I according to claim 1, wherein:
m is 1;
n is 1;
A is a single bond or a straight-chained or branched $C_{1-6}$-alkylene group;
$R^1$ is a straight-chained or branched $C_{1-6}$-alkyl group,
$R^2$ is a hydrogen atom, a straight-chained or branched $C_{1-6}$-alkyl group which is optionally substituted by a hydroxy group, a $C_{1-4}$-alkenyl group or a $C_{1-4}$-alkynyl group, wherein the hydroxy group is not bound in the 1 position and the multiple bond is isolated from the nitrogen-carbon bond, or
$R^1$ and $R^2$ together with the nitrogen atom are a 5- to 7-membered, saturated heterocyclic ring wherein a methylene group isolated from the nitrogen atom is optionally replaced by an oxygen atom;
$R^3$ to $R^6$, which are identical or different, are hydrogen atoms or methyl groups;
$R^7$ is a straight-chained or branched $C_{1-6}$-alkyl group or a $C_{1-4}$-alkenyl group, wherein the multiple bond is isolated from the nitrogen-carbon bond; and
$R^8$ is a $C_{3-6}$-cycloalkyl group, a phenyl or naphthyl group optionally substituted by one or two halogen atoms or by an alkyl, alkoxy, trifluoromethyl or cyano group,
wherein, unless otherwise stated, alkyl groups contained in the groups mentioned above each contain 1 to 3 carbon atoms and a halogen atom mentioned above is a fluorine, chlorine, or bromine atom,
or a pharmaceutically acceptable salt thereof.
3. The compound of general formula I according to claim 2, wherein;
A is a single bond or a methylene group;
$R^1$ is a methyl or ethyl group,
$R^2$ is a methyl, ethyl, allyl, or propargyl group, or
$R^1$ and $R^2$ together with the nitrogen atom are a pyrrolidine or piperidine ring;
$R^3$ to $R^6$ are hydrogen atoms;
$R^7$ is a methyl group; and
$R^8$ is a phenyl group optionally substituted by a chlorine or fluorine atom or by a methyl group,
or a pharmaceutically acceptable salt thereof.
4. A compound selected from the group consisting of:

(a) trans-S-(4-chlorophenyl)-N-4-[4-(dimethylaminomethyl)-phenyl]cyclohexyl-N-methyldithiocarbamate;
(b) trans-S-(3-fluorobenzyl)-N-4-[4-(dimethylaminomethyl)-phenyl]cyclohexyl-N-methyldithiocarbamate;
(c) trans-S-(4-fluorobenzyl)-N-4-[4-(dimethylaminomethyl)-phenyl]cyclohexyl-N-methyldithiocarbamate;
(d) trans-S-(4-chlorobenzyl)-N-4-[4-(dimethylaminomethyl)-phenyl]cyclohexyl-N-methyldithiocarbamate;
(e) trans-O-(4-chlorophenyl)-N-4-[4-(dimethylaminomethyl)-phenyl]cyclohexyl-N-methylcarbamate;
(f) cis-S-benzyl-N-4-[4-(dimethylaminomethyl)phenyl]-cyclohexyl-N-methyldithiocarbamate;
(g) trans-O-(4-chlorophenyl)-N-4-[4-(dimethylaminomethyl)-phenyl]cyclohexyl-N-methylthiocarbamate;
(h) trans-S-(4-chlorophenyl)-N-4-[4-(dimethylaminomethyl)-phenyl]cyclohexyl-N-methylthiocarbamate;
(i) trans-O-(4-chlorophenyl)-N-methyl-N-4-[4-(piperidinomethyl)phenyl]cyclohexylcarbamate;
(j) trans-O-(4-chlorophenyl)-N-methyl-N-4-[4-(pyrrolidinomethyl)phenyl]cyclohexylcarbamate;
(k) trans-O-(4-chlorophenyl)-N-4-[4-(diethylaminomethyl)-phenyl]cyclohexyl-N-methylcarbamate;
(l) trans-O-(4-chlorophenyl)-N-methyl-N-4-[4-(N-methyl-N-allylaminomethyl)phenyl]cyclohexylcarbamate;
(m) trans-O-(4-chlorophenyl)-N-methyl-N-4-[4-(N-methyl-N-propargylaminomethyl)phenyl]cyclohexylcarbamate;
(n) trans-N-4-[4-(dimethylaminomethyl)phenyl]cyclohexyl-N-methyl-O-(4-methylphenyl)carbamate;

(o) trans-N-4-[4-(dimethylaminomethyl)phenyl]cyclohexyl-N-methyl-O-(4-methylphenyl)thiocarbamate;

(p) trans-N-methyl-O-(4-methylphenyl)-N-4-[4-(piperidino-methyl)phenyl]cyclohexylthiocarbamate; and (q) trans-N-4-[4-(dimethylaminomethyl)phenyl]cyclohexyl-O-(4-fluorophenyl)-N-methylcarbamate;

or a pharmaceutically acceptable salt thereof.

5. A compound of general formula I:

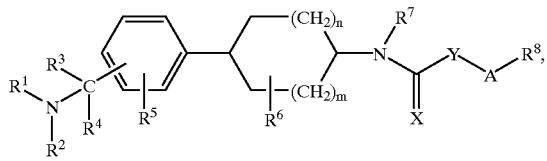

(I)

wherein:

m is 0 or 1;

n is 1 or 2;

A is a single bond, a straight-chained or branched $C_{1-8}$-alkylene group, a $C_{2-8}$-alkenylene or $C_{2-8}$-alkynylene group, wherein an unsaturated group is not directly bound to the group Y;

X is a sulfur atom;

Y is an oxygen or sulfur atom;

$R^1$ is a straight-chained or branched $C_{1-8}$-alkyl group, a $C_{1-6}$-alkenyl group, or a $C_{1-6}$-alkynyl group, wherein the multiple bond is isolated from the nitrogen-carbon bond, $R^2$ is a hydrogen atom, a straight-chained or branched $C_{1-8}$-alkyl group which is optionally substituted by a hydroxy or alkoxy group, a $C_{1-6}$-alkenyl group or a $C_{1-6}$-alkynyl group, wherein a hydroxy and alkoxy substituent is not bound in the 1-position and a multiple bond is isolated from the nitrogen-carbon bond, or $R^1$ and $R^2$ together with the nitrogen atom are a 5- to 7-membered, saturated heterocyclic ring wherein a methylene group isolated from the nitrogen atom is optionally replaced by an oxygen or sulfur atom or by an —NH— or —N(alkyl)- group;

$R^3$ to $R^6$, which are identical or different, are hydrogen atoms or alkyl groups;

$R^7$ is a straight-chained or branched $C_{1-6}$-alkyl group, a $C_{1-6}$-alkenyl group or a $C_{1-6}$-alkynyl group, wherein the multiple bond is isolated from the nitrogen-carbon bond; and $R^8$ is a $C_{3-7}$-cycloalkyl group, a phenyl or naphthyl group optionally substituted by one or two halogen atoms or by an alkyl, alkoxy, trifluoromethyl, or cyano group or, if A is not a single bond, $R^8$ also is a hydrogen atom, wherein, unless otherwise stated, alkyl groups contained in the groups mentioned above each contain 1 to 3 carbon atoms and a halogen atom mentioned above is a fluorine, chlorine, or bromine atom, or a pharmaceutically acceptable salt thereof.

6. The compound of general formula I according to claim 13, wherein:

m is 1;

n is 1;

A is a single bond or a straight-chained or branched $C_{1-6}$-alkylene group;

$R^1$ is a straight-chained or branched $C_{1-6}$-alkyl group, $R^2$ is a hydrogen atom, a straight-chained or branched $C_{1-6}$-alkyl group which is optionally substituted by a hydroxy group, a $C_{1-4}$-alkenyl group or a $C_{1-4}$-alkynyl group, wherein the hydroxy group is not bound in the 1 position and the multiple bond is isolated from the nitrogen-carbon bond, or $R^1$ and $R^2$ together with the nitrogen atom are a 5- to 7-membered, saturated heterocyclic ring wherein a methylene group isolated from the nitrogen atom is optionally replaced by an oxygen atom;

$R^3$ to $R^6$, which are identical or different, are hydrogen atoms or methyl groups;

$R^7$ is a straight-chained or branched $C_{1-6}$-alkyl group or a $C_{1-4}$-alkenyl group, wherein the multiple bond is isolated from the nitrogen-carbon bond; and $R^8$ is a $C_{3-6}$-cycloalkyl group, a phenyl or naphthyl group optionally substituted by one or two halogen atoms or by an alkyl, alkoxy, trifluoromethyl or cyano group or, if A is not a single bond, $R^8$ also is a hydrogen atom, wherein, unless otherwise stated, alkyl groups contained in the groups mentioned above each contain 1 to 3 carbon atoms and a halogen atom mentioned above is a fluorine, chlorine, or bromine atom, or a pharmaceutically acceptable salt thereof.

7. The compound of general formula I according to claim 14, wherein;

A is a single bond or a methylene group;

$R^1$ is a methyl or ethyl group, $R^2$ is a methyl, ethyl, allyl, or propargyl group, or $R^1$ and $R^2$ together with the nitrogen atom are a pyrrolidine or piperidine ring;

$R^3$ to $R^6$ are hydrogen atoms;

$R^7$ is a methyl group; and $R^8$ is a phenyl group optionally substituted by a chlorine or fluorine atom or by a methyl group, or a pharmaceutically acceptable salt thereof.

8. A compound of general formula I:

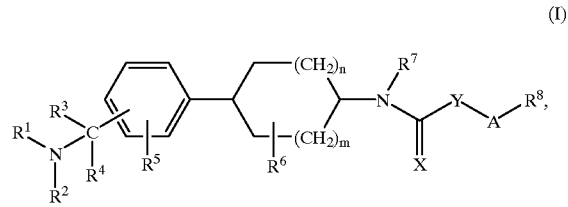

(I)

wherein:

m is 0 or 1;

n is 1 or 2;

A is a single bond, a straight-chained or branched $C_{1-8}$-alkylene group, a $C_{2-8}$-alkenylene or $C_{2-8}$-alkynylene group, wherein an unsaturated group is not directly bound to the group Y;

X is an oxygen or sulfur atom;

Y is a sulfur atom;

$R^1$ is a straight-chained or branched $C_{1-8}$-alkyl group, a $C_{1-6}$-alkenyl group, or a $C_{1-6}$-alkynyl group, wherein the multiple bond is isolated from the nitrogen-carbon bond, $R^2$ is a hydrogen atom, a straight-chained or branched $C_{1-8}$-alkyl group which is optionally substituted by a hydroxy or alkoxy group, a $C_{1-6}$-alkenyl group or a $C_{1-6}$-alkynyl group, wherein a hydroxy and alkoxy substituent is not bound in the 1-position and a multiple bond is isolated from the nitrogen-carbon bond, or $R^1$ and $R^2$ together with the nitrogen atom are a 5- to 7-membered, saturated heterocyclic ring wherein a methylene group isolated from the nitrogen atom is optionally replaced by an oxygen or sulfur atom or by an —NH— or —N(alkyl)- group;

$R^3$ to $R^6$, which are identical or different, are hydrogen atoms or alkyl groups;

$R^7$ is a straight-chained or branched $C_{1-6}$-alkyl group, a $C_{1-6}$-alkenyl group or a $C_{1-6}$-alkynyl group, wherein the multiple bond is isolated from the nitrogen-carbon bond; and $R^8$ is a $C_{3-7}$-cycloalkyl group, a phenyl or naphthyl group optionally substituted by one or two halogen atoms or by an alkyl, alkoxy, trifluoromethyl, or cyano group or, if A is not a single bond, $R^8$ also is a hydrogen atom, wherein, unless otherwise stated, alkyl groups contained in the groups mentioned above each contain 1 to 3 carbon atoms and a halogen atom mentioned above is a fluorine, chlorine, or bromine atom, or a pharmaceutically acceptable salt thereof.

9. The compound of general formula I according to claim 8, wherein:

m is 1;

n is 1;

A is a single bond or a straight-chained or branched $C_{1-6}$-alkylene group;

$R^1$ is a straight-chained or branched $C_{1-6}$-alkyl group, $R^2$ is a hydrogen atom, a straight-chained or branched $C_{1-6}$-alkyl group which is optionally substituted by a hydroxy group, a $C_{1-4}$-alkenyl group or a $C_{1-4}$-alkynyl group, wherein the hydroxy group is not bound in the 1 position and the multiple bond is isolated from the nitrogen-carbon bond, or $R^1$ and $R^2$ together with the nitrogen atom are a 5- to 7-membered, saturated heterocyclic ring wherein a methylene group isolated from the nitrogen atom is optionally replaced by an oxygen atom;

$R^3$ to $R^6$, which are identical or different, are hydrogen atoms or methyl groups;

$R^7$ is a straight-chained or branched $C_{1-6}$-alkyl group or a $C_{1-4}$-alkenyl group, wherein the multiple bond is isolated from the nitrogen-carbon bond; and $R^8$ is a $C_{3-6}$-cycloalkyl group, a phenyl or naphthyl group optionally substituted by one or two halogen atoms or by an alkyl, alkoxy, trifluoromethyl or cyano group or, if A is not a single bond, $R^8$ also is a hydrogen atom, wherein, unless otherwise stated, alkyl groups contained in the groups mentioned above each contain 1 to 3 carbon atoms and a halogen atom mentioned above is a fluorine, chlorine, or bromine atom, or a pharmaceutically acceptable salt thereof.

10. The compound of general formula I according to claim 11, wherein;

A is a single bond or a methylene group;

$R^1$ is a methyl or ethyl group, $R^2$ is a methyl, ethyl, allyl, or propargyl group, or $R^1$ and $R^2$ together with the nitrogen atom are a pyrrolidine or piperidine ring;

$R^3$ to $R^6$ are hydrogen atoms;

$R^7$ is a methyl group; and $R^8$ is a phenyl group optionally substituted by a chlorine or fluorine atom or by a methyl group, or a pharmaceutically acceptable salt thereof.

11. The pharmaceutical composition containing a cholesterol biosynthesis inhibiting amount of a compound in accordance with one of claims 1, 2, 3, 4, 5, 6, 7, 8, 9, or 10.

12. The pharmaceutical compositions according to claim 11, further comprising an additional active substance with a cholesterol- or lipid-lowering activity.

13. The pharmaceutical composition according to claim 12, wherein the additional active substance with a cholesterol- or lipid-lowering activity is selected from the group consisting of:

resins which bind bile acid;

compounds which inhibit cholesterol absorption;

compounds which are involved in cholesterol biosynthesis by a mechanism other than the inhibition of 2,3-epoxysqualene-lanosterol-cyclase;

fibrates;

nicotinic acid, the derivatives and analogues thereof; and probucol.

14. A method for the treatment or prophylaxis of hypercholesterolaemia, hyperlipoproteinaemia, hypertriglyceridaemia and the resulting atherosclerotic vascular changes with their consequent diseases selected from the group consisting of coronary heart disease, cerebral ischaemia, Claudicatio intermittens and gangrene, the method comprising administering to a host in need of such prophylaxis or treatment a therapeutic amount of a compound in accordance with one of claims 1, 2, 3, 4, 5, 6, 7, 8, 9, or 10.

15. A method for the treatment of gallstones, the method comprising administering to a host in need of such treatment a therapeutic amount of a compound in accordance with one of claims 1, 2, 3, or 4.

16. A method for the treatment of mycoses, the method comprising administering to a host in need of such treatment a therapeutic amount of a compound in accordance with one of claims 1, 2, 3, or 4.

17. Feed for laying hens, containing a compound according to one of claims 1, 2, 3, or 4.

18. A method for inducing hens to lay low-cholesterol eggs, the method comprising administering to the hens a cholesterol biosynthesis inhibiting amount of a compound in accordance with one of claims 1, 2, 3, or 4.

19. The compound trans-N-4-[4-(dimethylaminomethyl)phenyl]cyclohexyl-O-(4-fluorophenyl)-N-methylcarbamate, or a pharmaceutically acceptable salt thereof.

* * * * *

UNITED STATES PATENT AND TRADEMARK OFFICE
CERTIFICATE OF CORRECTION

PATENT NO. : 6,346,545 B1
DATED : February 12, 2002
INVENTOR(S) : Roland Maier, Rudolf Hurnaus, Michael Mark, Bernhard Eisele, Peter Mueller, Gebhard Adelgoss and Gebhard Schilcher It is certified that error appears in the above-identified patent and that said Letters Patent is hereby corrected as shown below:

Title page,
The *Primary Examiner*, given as "Ceila Chang" should read -- Celia Chang --.

Column 17,
Line 28, "anmals" should read -- animals --.

Column 27,
Line 61, "according to claim 13 wherein;" should read -- according to claim 5 wherein: --

Column 28,
Line 27, "according to claim 14 wherein;" should read -- according to claim 6 wherein: --

Column 29,
Line 59, "according to claim 11 wherein;" should read -- according to claim 9 wherein: --

Signed and Sealed this

Twenty-fourth Day of September, 2002

Attest:

*Attesting Officer*

JAMES E. ROGAN
*Director of the United States Patent and Trademark Office*